United States Patent
Searfoss et al.

[11] Patent Number: 5,265,598
[45] Date of Patent: Nov. 30, 1993

[54] PHOTOTHERAPY METHOD

[75] Inventors: John Searfoss, Marshall, Mo.; Robert L. Searfoss, III, Atlanta, Ga.

[73] Assignee: Energy Spectrum Foundation, Atlanta, Ga.

[21] Appl. No.: 730,685

[22] Filed: Jul. 16, 1991

Related U.S. Application Data

[63] Continuation-in-part of Ser. No. 573,531, Aug. 27, 1990, Pat. No. 5,046,494.

[51] Int. Cl.$^5$ .............................................. A61N 5/00
[52] U.S. Cl. ............................................ 607/88; 600/27
[58] Field of Search .............................. 128/395–398, 128/633, 653 R, 653 A, 783, 793, 732

[56] References Cited

U.S. PATENT DOCUMENTS

| | | | |
|---|---|---|---|
| 3,998,209 | 12/1976 | Macvaugh | 600/27 |
| 4,140,997 | 2/1979 | Brady | 128/732 |
| 4,289,121 | 9/1981 | Kupyiyanovich | 600/27 |
| 4,315,502 | 2/1982 | Gorges | 600/27 |
| 4,632,126 | 12/1986 | Aguilar | 128/732 |
| 5,036,858 | 8/1991 | Carter | 600/27 |
| 5,064,410 | 11/1991 | Frenkel et al. | 600/27 |

FOREIGN PATENT DOCUMENTS 375106  6/1990  European Pat. Off. ............ 128/732

*Primary Examiner*—Mark S. Graham
*Attorney, Agent, or Firm*—Fulwider, Patton, Lee & Utecht

[57] ABSTRACT

A phototherapy method wherein sequences of various substantially isolated electromagnetic energy patterns are directed into an observer's eyes in order to determine to which such pattern the observer is most responsive in terms of being induced towards a state of homeostasis. Subsequent irradiation of the observer's eyes with such pattern will bring about therapeutic effects in the observer.

9 Claims, 1 Drawing Sheet

PHOTOTHERAPY METHOD

This application is a Continuation-in-Part of application Ser. No. 07/573,531 filed Aug. 27, 1990, now U.S. Pat. No. 5,046,494.

BACKGROUND OF THE INVENTION

1. Field of the Invention

The present invention relates to phototherapy techniques and more particularly pertains to methods for maximizing the therapeutic effect that electromagnetic radiation can have on the body and the mind.

2. Description of the Prior Art

It has long been recognized that light can have profound psychological as well as physiological effects on the human organism. Although both ocular as well as non-ocular techniques have been employed in an attempt to achieve various such effects, ocular treatment appears to be most efficacious. The retinas do after all avail most of the body's blood supply to substantially direct irradiation in a very short period of time due to the high rate of blood flow therethrough and due to the density and proximity of the capillaries to the retina's surface. Furthermore, not only are the eyes highly specialized organs specifically adapted for receiving and sensing light, but a sizable portion of the brain is exclusively devoted to processing data generated by the retinas. Moreover, neurologists and anatomists have relatively recently demonstrated the existence of nerve pathways extending from the retinas that are separate and apart from the pathways linked to the sight center of the brain. These newly discovered interconnections link the eyes with neurological centers in the brain that influence and control many of the body's regulatory functions. Such regulatory centers typically exert their control via neurological or biochemical means.

An example of an organ whose regulatory function is responsive to light sensed by the eyes is the pineal gland which secretes the hormone melatonin. The hormone is released during periods of darkness while production is abruptly halted when the eyes perceive bright light. Melatonin is distributed throughout the body via the blood and cerebrospinal fluid and can effect the function of organs by which it is metabolized to thereby influence sleep cycles, feeding cycles, reproduction cycles and other biological rhythms. It has therefore been suggested that phototherapy may effectively be employed to correct a melatonin imbalance which may have resulted from, for example, shift work, jet lag or life in the polar regions, and thereby remedy the accompanying symptoms.

Other such relationships have been discovered, more are suspected and even more may, in fact, exist. Additionally, it has been found that some of the body's responses to light are acutely dependent upon specific characteristics of the light received by the eyes such as the light's wavelength, and intensity, and further, that particular responses can be elicited or enhanced by varying such characteristics according to certain sequences or patterns. Although instruments have been constructed and techniques devised to generally exploit this systemic sensitivity to light, many important factors had not been taken into consideration as required in order to take fuller advantage of the effect of electromagnetic radiation on the human organism. The present invention seeks to overcome some of these shortcomings.

SUMMARY OF THE INVENTION

Applicants have found that an individual's physiological and psychological state is especially responsive to only certain, very specific electromagnetic energy patterns and that such responses are heightened and in fact some such responses are only achievable by substantially isolating the patterns that have been found to be effective from ineffective patterns. By directing substantially isolated effective patterns into an individual's eyes for relatively short periods of time, relatively long-lasting therapeutic effects are realizable. "Energy pattern" is used herein as a very broad term and refers to any recognizable order, arrangement, distribution or other characteristics associated with electromagnetic energy radiation, including for example the fundamental frequency associated with a particular wavelength, radiation intensity, patterns of radiation intensity variation over time, the polarization and coherence of radiation, and the spatial configuration of an image produced by the electromagnetic radiation. Energy patterns useful for the purposes of the present invention range from the extremely simple and pure, such as substantially monochromatic radiation of constant intensity, to complex composites of patterns such as for example the pulsing of multichromatic radiation, gradually increasing in terms of pulse frequency, image size, and intensity. The specific patterns which elicit desired responses in individuals, have been found to vary from individual to individual and have been found to vary for a particular individual over time. The methods in accordance with the present invention take advantage of this discovery to provide a form of therapy for a wide variety of disorders or irregularities.

It has been found that a variety of long-lasting therapeutic effects are achievable by inducing an individual to enter into or assume an apparently relaxed, nominally homeostatic state as a direct result of the exposure of the individual's eyes to the selected electromagnetic energy patterns for a relatively short period of time. Such long-lasting therapeutic effects which include some of the readily apparent indications of the homeostatic state induced by the irradiation include, but are not limited to, a normalization of vital signs such as blood pressure, respiration rate and heart rate, regulation and stabilization of hormonal levels, normalization of blood imbalances, stimulation of the immune system by enhancement of the regenerative processes, increase of the efficiency of motor coordination and action, reduction and balance of local and systemic edema, normalization of intra-ocular pressure, stabilization of emotions, increase of psychological awareness, mental clarity and concentration, increase of peripheral vision, and resolution of migraine headaches.

The method according to the invention first calls for the identification of a particular electromagnetic energy pattern which has an apparently homeostasis inducing effect on a particular individual and then directing radiation of such form into the individual's eyes for a preselected period of time. It has been found that by isolating the individual from extraneous sensory input, an individual's responsiveness is further enhanced and that a final exposure to electromagnetic energy perceived as generally green in color, followed by a gradual reintroduction to ambient lighting, sounds and other environmental influences at the end of each therapy session tends to further extend or preserve the effect. Additionally, it may be necessary to adjust or retune the energy pattern to compensate for an individual's change in responsiveness either during a particular session or with the commencement of a new session.

Monochromatic radiation of constant intensity represents a very pure and a most fundamental of energy patterns. More complex patterns are generated by expanding the bandwidth or otherwise combining wavelengths, or by varying intensity either as a function of wavelength or time. For example, in contrast to a monochrome, a band of the electromagnetic spectrum is definable in terms of bandwidth, median wavelength and area.

By additionally varying intensity as function of wavelength, such terms as distribution, shape and peak acquire significance. Repetitive variation of intensity as a function of time results in a pulsing or undulation which is definable in terms of a pulse or undulation rate, rise time, fall rate, peak time, valley time, and perhaps a step rate and size. Many such parameters, either singly or in combination with other such parameters, yield energy patterns especially effective for the purposes of this invention. Additional exploitable parameters pertaining to electromagnetic radiation are the radiation's polarization and coherence as well as the spatial configuration of an image formed by electromagnetic radiation as presented to an observer's eyes.

In order to identify the specific energy pattern to which a particular individual, at a particular moment in time is most responsive, the individual is monitored with respect to indications of homeostasis while a sequence of specific energy patterns is radiated directly into the individual's eyes. Homeostatic response is manifested by, among other things, a normalization of heart rate, respiration rate, blood pressure, body temperature, muscle tension, intra ocular pressure, ocular tear secretion rate, motor activity, a shift in galvanic skin response, or a shift of the brain waves towards theta. Monitoring any one or a combination of the relevant functions can facilitate the identification of a particular stimulus that has the desired homeostasis-inducing effect. Additionally, or alternatively the individual's own subjective perceptions are relied upon during the identification efforts. A perceived feeling of well-being, relaxation or the experiencing of a soothing sensation has proven to be a useful indicator of entry into a more advanced homeostatic state. The energy pattern of a particular sequence having the most pronounced such effect is then employed directly as a therapeutic tool or as a basis for identifying more complex combinations of patterns to yield a potentially even greater effect.

The method of the present invention does not require full understanding of the mechanisms that cause certain energy patterns to evoke psychological and physiological responses. The method relies on a substantially empirical approach wherein a particular energy pattern is exploited because it induces homeostatic response without regard to why or how. It has been found that individuals are at first typically most responsive to fairly fundamental, simple, or pure patterns and it is for this reason that substantially monochromatic or narrow wavebands of radiation are preferred initially. It has additionally been found that as a particular individual becomes more accustomed to this type of phototherapy, responsiveness to more complex patterns gradually increases. The electromagnetic energy range employed need not be limited to the visible spectrum, but can extend into wavelengths not consciously perceived by the individual. Indeed, many of the more intricate and subtler patterns involving for example certain waveband contours or intensity pulse profiles and timing have been found to affect individuals subconsciously.

An additional technique that has been found to facilitate the identification of the most effective energy patterns is the presentation of the various patterns in a generally energy-increasing sequence. For example, in order to identify the wavelengths to which an individual is most responsive, a sequence of narrow wavebands is presented progressing from low energy, long wavelengths toward high energy, short wavelength. Similarly, in order to determine the most effective intensity, a sequence from low intensity to higher intensity is preferred. Pulse rates, rise times, image size, as well as most parameters associated with electromagnetic radiation are arrangable in an energy-increasing sequence for this purpose. The parameters of coherence and polarization are preferably varied in sequences extending from a random distribution to a more highly ordered pattern.

Other features and advantages of the present invention will become apparent from the following detailed description of the preferred embodiments which illustrate by way of example the principles of the invention.

DETAILED DESCRIPTION OF THE PREFERRED EMBODIMENTS

The following describes a method by which effective electromagnetic energy patterns are first identified and subsequently used as a therapeutic tool. The method requires electromagnetic energy to be radiated directly into an observer's eyes but is not limited to wavelengths in the visible spectrum. When the eyes are irradiated with the effective energy pattern(s) during a session, a multi-faceted, long-lasting therapeutic response results.

In order to practice the present invention, means are required for selectably directing specific bands of electromagnetic energy directly into an observer's eyes. It is additionally preferable that the intensity of such wavebands is selectably variable. It has been found that individuals are responsive to very specific energy patterns and that response is diminished if ineffective patterns are included in a particular composite of energy patterns. Such diminution may be the result of dilution, distraction, interference, or other factors.

In order to therefore provide as "pure" an energy pattern as possible, both in an effort to identify an effective pattern and then to maximize the efficacy of such pattern to achieve therapeutic results, the use of substantially monochromatic or relatively narrow wavebands is required. Narrow band pass filters are currently available that facilitate the selection of a variety of such narrow wavebands (10–20 nm) throughout the electromagnetic spectrum from a single radiation source.

Additionally, in order to eliminate the 50 or 60 Hz pattern component that would automatically be incorporated in an energy pattern composite with the use of an AC powered radiation source, a DC powered radiation source is preferably employed. For more complex embodiments of the present invention, the intensity of such source should be readily selectively alterable over time, such that wave patterns can be created that are variable in terms of pulse rate, peak voltage, peak time, rise time, fall time, and valley time. Power supply wave generators capable of providing such versatility are commercially available.

An additionally readily variable parameter associated with directing electromagnetic radiation into an observer's eyes is the apparent size and shape of the field of radiation. Finally, by integrating two separate systems side by side, each directing radiation to a single eye, even more versatility is available to enable identification of a particular pattern to which an individual is most responsive and to then avail such pattern for administration of the therapy. Such a system allows monocular, binocular, or biocular presentation of the various energy patterns. Additionally, the capability to vary the polarization and coherence of electromagnetic radiation can be included for exploitation in accordance with the method of the present invention.

Figure 1:
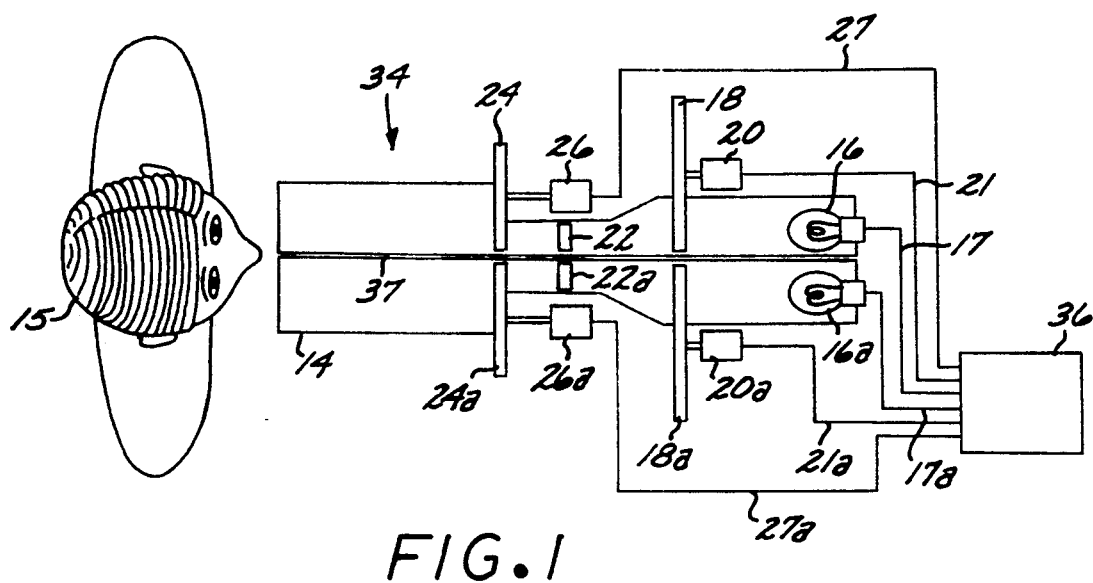
FIG. 1 is a schematic representation of an apparatus used for practicing the methods of the present invention.
Figure 2:
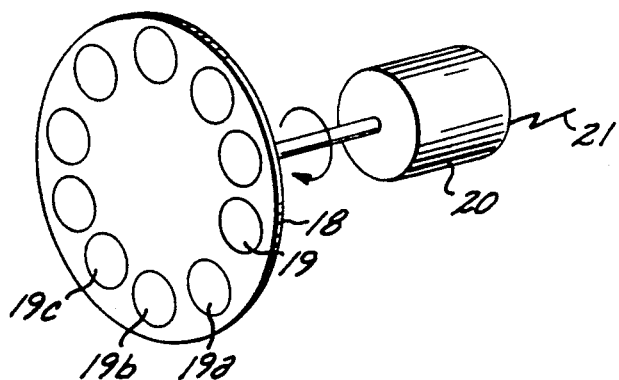
FIGS. 2 & 3 are perspective representations of components of the device illustrated in FIG. 1.
Figure 3:
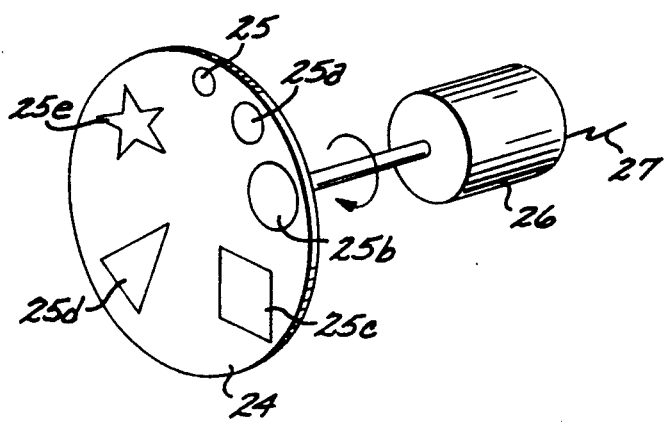

FIG. 1 illustrates an apparatus which provides much of the versatility described above. The phototherapy apparatus 34 provides independently variable displays of electromagnetic radiation to each eye of an observer 15. Hooded section 14 is configured and positioned such that an observer 15 can comfortably gaze thereinto. Two independently controllable radiation sources 16, 16a are placed at the opposite end of the device. Each radiation source 16, 16a preferably comprises a DC powered incandescent device interconnected to controller 36 via conduits 17, 17a. Controller 36 incorporates two independently controllable power supplies, each comprising a fully adjustable wave generator that facilitates adjustment of the resulting wave form in terms of peak height, wave length, rise time, peak time, fall time, valley time, wave area, wave shape, etc. Radiation generated by radiation sources 16, 16a is subsequently filtered through narrow band pass filters 19 arranged on filter discs 18, 18a, the rotation of which selectably alters the radiation directed towards the observer's eyes. Servo motors 20, 20a rotate discs 18, 18a in response to a signal generated by controller 36 and received via conduits 21, 21a. Radiation passing through the selected filter is subsequently diffused in diffusers 22, 22a. While ground glass plates are preferred, integrating spheres are alternatively used to achieve the desired homogeneous field of radiation.

The diffused radiation then passes through a selected one of a number of apertures 25. A plurality of different size and shape apertures are accommodated on each aperture disc 24, 24a rotatable by servo motors 26, 26a that are responsive to signals from controller 36 communicated via conduits 27, 27a. An assortment of apertures 25, 25a, 25b increase the amount of light transmitted while apertures 25c, 25d, 35e provide an assortment of shapes.

By controlling the voltage supplied to radiation sources 16, 16a, the positions of filter discs 18, 18a and the position of aperture discs 24, 24a two precisely controllable displays of radiation are directed into the observer's eyes. Barrier 37 segregates the two displays such that monocular or biocular displays are possible.

The preferred method of practicing the present invention in its most basic form involves binocular treatment, the use of narrow wavebands of radiation selected from throughout the visible spectrum corresponding to what are perceived as eight different colors evenly spaced throughout such spectrum, and relies on the observer's own subjective selections vis-a-vis the most homeostatic effect. The observer is first isolated from distractions such as extraneous light and sound and postural stresses are minimized to allow the individual to properly concentrate on the display directed into the eyes while peering into the device described above.

An intermediate intensity is selected and the wavebands are displayed one at a time progressing from the relatively long to the shorter wavelengths for about 3-5 minutes each. The intensity remains constant throughout the session. The observer is asked to identify the three wavebands which have the most soothing effect. Those three wavebands are then redisplayed 5-8 minutes at a time, again in a long wavelength to short wavelength sequence. The observer is asked to narrow his preference down to two and then one waveband. Once identified, the waveband found to be most soothing is displayed for about twenty minutes. Subsequent thereto, an intermediate waveband such as corresponding to a color perceived as green is displayed for a few minutes after which ambient lighting is gradually phased in to complete the session.

More complex methods of practicing the present invention expand on the above described sequence. For example, once a preferred waveband has been selected, the intensity of such waveband is varied in an increasing sequence to enable the observer to identify the intensity found to be most soothing. The preferred values of the other variable parameters are selected in a similar manner. A preferred waveband at a preferred intensity is then pulsed in a sequence of varying pulse rates in order to identify a pattern of increased complexity and effectiveness. The other capabilities of the above described device are similarly explored in terms of their effect on the particular individual. Eventually, a potentially very complex energy pattern is composed to which a particular individual is particularly responsive.

Alternatively, instead of relying on the observer's subjective perceptions as to which energy pattern offers the most homeostasis inducing effect, more objective indications are relied upon. By monitoring physiological responses such as the observer's heart or respiration rates during the sequential display of various patterns, an enhanced state of homeostasis is immediately recognizable. Real time monitoring of blood pressure or body temperature provide similar indications. Monitoring an EEG for a shift toward theta has been similarly found to be useful. Other functions that provide indications of homeostasis in the organism include galvanic skin response, muscle tension, intra ocular pressure, ocular tear secretion rate and motor activity.

While a particular form of the invention has been illustrated and described, it will also be apparent to those skilled in the art that various modifications can be made both to the apparatus as well as to the methods employed without departing from the spirit and scope of the invention. Accordingly it is not intended that the invention be limited except as by the appended claims.

What is claimed is:

1. A method for achieving therapeutic effects in an observer, comprising the steps of:
   selecting a variable parameter relating to electromagnetic radiation wherein said electromagnetic radiation is substantially monochromatic having a bandwidth of no more than about 20 nm and wherein, the variation of said parameter serves to alter the electromagnetic energy pattern associated with such radiation;
   directing said electromagnetic radiation towards an observer's eyes while varying said selected parameter and monitoring said observer's state for homeostatic responses;

identifying a value of said selected parameter most effective in eliciting a homeostatic response in said observer; and directing said electromagnetic radiation towards said observer's eyes while maintaining said selected parameter constant at said identified value for a predetermined period of time whereby therapeutic effects are achieved in the observer.

2. The method of claim 1, wherein said variable parameters are selected from the group consisting of wavelength, wavelength distribution, intensity, apparent field size, image shape, intensity fluctuation rate, peak time, rise time, fall time, valley time, polarization and coherence.

3. The method of claim 1, wherein said observer's state is monitored for homeostatic responses as a function of responses selected from the group consisting of heart rate normalization, respiration rate normalization, blood pressure normalization, galvanic skin response, muscle tension normalization, intra ocular pressure normalization, brain wave shift toward theta, body temperature normalization, ocular tear secretion rate normalization, and motor activity normalization.

4. The method of claim 1, further comprising the steps of:

directing a substantially monochromatic electromagnetic waveband perceived as green light towards said observer's eyes after said predetermined period of time; and then gradually phasing in ambient lighting.

5. The method of claim 1 further comprising the steps of:

selecting additional parameters relating to electromagnetic radiation, the variation of which serves to alter the electromagnetic energy pattern associated with such radiation;

identifying a value associated with each such additional parameter most effective in eliciting a homeostatic response in said observer by monitoring said observer's state as each such additional parameter is varied, one such additional parameter at a time; and directing electromagnetic radiation toward said observer's eyes while holding said selected additional parameters constant at said identified values for a predetermined period of time.

6. The method of claim 5, further comprising the steps of:

directing a substantially monochromatic electromagnetic waveband perceived as green light towards said observer's eyes after said predetermined period of time; and then gradually phasing in ambient lighting.

7. The method of claim 1 wherein said selected parameter is varied in a generally energy increasing sequence.

8. The method of claim 1 wherein said electromagnetic radiation is generated by a DC power source.

9. A method for achieving therapeutic effects in an observer, comprising the steps of:

selecting a plurality of variable parameters relating to electromagnetic radiation, the variation of each of such parameters serving to alter the electromagnetic energy pattern associated with such radiation;

directing electromagnetic radiation towards an observer's eyes while varying one said selected parameter at a time and monitoring said observer's state for homeostatic responses;

identifying a value of each of said selected parameters most effective in eliciting a homeostatic response in said observer;

directing electromagnetic radiation towards said observer's eyes while maintaining said selected parameters constant at said identified values for a predetermined period of time whereby therapeutic effects are achieved in the observer;

directing a substantially monochromatic electromagnetic waveband perceived as green light towards said observer's eyes after said predetermined period of time; and then gradually phasing in ambient lighting.

* * * * *